United States Patent
Alberich Bayarri et al.

(10) Patent No.: US 11,915,420 B2
(45) Date of Patent: Feb. 27, 2024

(54) METHOD FOR OBTAINING AN IMAGE BIOMARKER THAT QUANTIFIES THE QUALITY OF THE TRABECULAR STRUCTURE OF BONES

(71) Applicants: Fundación para la Investigación del Hospital Universitario La Fe de la Comunidad Valenciana, Valencia (ES); QUIBIM, S.L., Valencia (ES); UNIVERSIDAD DE ZARAGOZA, Saragossa (ES)

(72) Inventors: Angel Alberich Bayarri, Valencia (ES); Fabio García Castro, Valencia (ES); Amadeo Ten Esteve, Valencia (ES); Luis Martí Bonmatí, Valencia (ES); María Ángeles Pérez Ansón, Saragossa (ES)

(73) Assignees: Fundación para la Investigación del Hospital Universitario La Fe de la Comunidad Valenciana, Valencia (ES); QUIBIM, S.L., Valencia (ES); UNIVERSIDAD DE ZARAGOZA, Saragossa (ES)

( * ) Notice: Subject to any disclaimer, the term of this patent is extended or adjusted under 35 U.S.C. 154(b) by 371 days.

(21) Appl. No.: 17/424,702

(22) PCT Filed: Jan. 17, 2020

(86) PCT No.: PCT/ES2020/070033
§ 371 (c)(1),
(2) Date: Jul. 21, 2021

(87) PCT Pub. No.: WO2021/105530
PCT Pub. Date: Jun. 3, 2021

(65) Prior Publication Data
US 2022/0084195 A1    Mar. 17, 2022

(30) Foreign Application Priority Data

Nov. 27, 2019 (ES) .................................. 201931050

(51) Int. Cl.
*G06T 7/00*       (2017.01)
*G06F 16/538*   (2019.01)
(Continued)

(52) U.S. Cl.
CPC .......... *G06T 7/0012* (2013.01); *G06F 16/538* (2019.01); *G06T 7/13* (2017.01);
(Continued)

(58) Field of Classification Search
CPC ......... G06T 7/0012; G06T 7/13; G06T 7/136; G06T 7/60; G06T 2207/10081;
(Continued)

(56) References Cited

U.S. PATENT DOCUMENTS

| 9,267,955 B2 * | 2/2016 | Lang ................... A61B 8/0875 |
| 2003/0088177 A1 * | 5/2003 | Totterman ................. G06T 7/12 600/414 |

(Continued)

OTHER PUBLICATIONS

Wehrli et al., "Noninvasive Assessment of Bone Architecture by Magnetic Resonance Micro-Imaging-Based Virtual Bone Biopsy", IEEE, Oct. 2003. (Year: 2003).*

(Continued)

*Primary Examiner* — Aaron W Carter
(74) *Attorney, Agent, or Firm* — Sughrue Mion, PLLC

(57) ABSTRACT

A method is disclosed for obtaining an image biomarker that quantifies the quality of the trabecular structure of bones. The method includes: retrieving high-resolution CT (Computed Tomography) and/or MRI (Magnetic Resonance Imaging) trabecular images from an image database; pre-processing and post-processing the high-resolution CT and/or MRI trabecular images and obtaining the unique image (Continued)

biomarker "QTS". Pre-processing may include: calculating the region of interest "ROI"; calculating the bone fraction map; eliminating the partial volume effect; and, binarizing. Post-processing may include: skeletonisation and extraction of morphological and structural characteristics. Lastly, the unique image biomarker "QTS" is defined as:

QTS=0.7137*Comp1+0.2863*Comp2.

**11 Claims, 4 Drawing Sheets
(1 of 4 Drawing Sheet(s) Filed in Color)**

(51) Int. Cl.
| | |
|---|---|
| *G06T 7/13* | (2017.01) |
| *G06T 7/136* | (2017.01) |
| *G06T 7/60* | (2017.01) |
| *G16H 30/40* | (2018.01) |

(52) U.S. Cl.
CPC ............... *G06T 7/136* (2017.01); *G06T 7/60* (2013.01); *G16H 30/40* (2018.01); *G06T 2207/10081* (2013.01); *G06T 2207/10088* (2013.01); *G06T 2207/20044* (2013.01); *G06T 2207/30008* (2013.01)

(58) Field of Classification Search
CPC . G06T 2207/10088; G06T 2207/20044; G06T 2207/30008; G06T 2207/20076; G06F 16/538; G16H 30/40; A61B 5/4509
See application file for complete search history.

(56) References Cited

U.S. PATENT DOCUMENTS

| | | | | |
|---|---|---|---|---|
| 2004/0114789 A1* | 6/2004 | Saha | ................... | G06T 7/62 |
| | | | | 382/128 |
| 2004/0147830 A1* | 7/2004 | Parker | ................ | A61B 6/463 |
| | | | | 600/407 |
| 2005/0010106 A1* | 1/2005 | Lang | ................ | A61B 6/4423 |
| | | | | 600/425 |
| 2007/0298998 A1* | 12/2007 | Paige | ................ | A61P 25/28 |
| | | | | 514/17.7 |
| 2012/0277571 A1* | 11/2012 | Cho | ................ | A61B 5/055 |
| | | | | 600/410 |
| 2015/0356730 A1* | 12/2015 | Grove | ................ | G06T 7/64 |
| | | | | 382/124 |
| 2022/0084195 A1* | 3/2022 | Alberich Bayarri | ... | G16H 30/40 |
| 2022/0343142 A1* | 10/2022 | Jiménez Pastor | ........ | G06N 3/08 |

OTHER PUBLICATIONS

Alberich-Bayarri et al., "In Vivo Trabecular Bone Morphologic and Mechanical Relationship Using High- Resolution 3-T Mri", American Journal of Roentgenology, 2008, pp. 721-726, vol. 191, No. 3.
Alberich-Bayarri et al., "Assessment of 2D and 3D fractal dimension measurements of trabecular bone from high- spatial resolution magnetic resonance images at 3 T", Med. Phys., 2010, pp. 4930-4937, vol. 37, No. 9.
Ascenzi et al., "Bone Tissue: Hierarchical Simulations for Clinical Applications", Journal of Biomechanics, 2011, pp. 211-212, vol. 44, No. 2.
Barkaoui et al., "Multiscale approach including microfibril scale to assess elastic constants of cortical bone based on neural network computation and homogenisation method", Int J Numer Method Bomed Eng., 2014, pp. 318-338, vol. 30, No. 3.
Boutroy et al., "In Vivo Assessment of Trabecular Bone Microarchitecture by High-Resolution Peripheral Quantitative Computed Tomography", The Journal of Clinical Endocrinology & Metabolism, 2005, pp. 6508-6515, vol. 90, No. 12.
"Box counting", Wikipedia, https://en.wikipedia.org/wiki/Box_counting, last updated Jun. 1, 2021.
Burkhart et al., "Finite element modeling mesh quality, energy balance and validation methods: A review with recommendations associated with the modeling of bone tissue", Journal of Biomechanics, 2013, pp. 1477-1488 Vol. 46.
Christen et al., "Multiscale modelling and nonlinear finite element analysis as clinical tools for the assessment of fracture risk", Phil. Trans. R. Soc. A, 2010, pp. 2653-2668, vol. 368.
"Convex combination", Wikipedia, https://en.wikipedia.org/wiki/Convex_combination, last updated Apr. 5, 2021.
Garcia-Aznar et al., "Computational simulation of fracture healing: Influence of interfragmentary movement on the callus growth", Journal of Biomechanics, 2007, pp. 1467-1476, vol. 40.
Gomez-Benito et al., "A 3D Computational Simulation of Fracture Callus Formation: Influence of the Stiffness of the External Fixator", Journal of Biomechanical Engineering, 2006, pp. 290-299, vol. 128.
Hambli et al., "Multiscale methodology for bone remodelling simulation using coupled finite element and neural network computation", Biomech Model Mechanobiol, 2011, pp. 133-145, vol. 10.
Hwang et al., "Subvoxel Processing: A Method for Reducing Partial Volume Blurring With Application to In Vivo MR Images of Trabecular Bone", Magnetic Resonance in Medicine, 2002, pp. 948-957, vol. 47.
Ito et al., "Multi-Detector Row CT Imaging of Vertebral Microstructure for Evaluation of Fracture Risk", Journal of Bone and Mineral Research, 2005, pp. 1828-1836, vol. 20.
Kazakia et al., "In Vivo Determination of Bone Structure in Postmenopausal Women: A Comparison of HR-pQCT and High-Field MR Imaging", Journal of Bone and Mineral Research, 2008, pp. 463-474, vol. 23.
Kuhn et al., "Neurogenesis in the Dentate Gyrus of the Adult Rat: Age-Related Decrease of Neuronal Progenitor Proliferation", The Journal of Neuroscience, 1996, pp. 2027-2033, vol. 16, No. 6.
Link, "Osteoporosis Imaging: State of the Art and Advanced Imaging", Radiology, 2012, pp. 3-17, vol. 263, No. 1.
"Mathematical morphology", Wikipedia, https://en.wikipedia.org/wiki/Mathematical_morphology, last updated May 12, 2021.
"Medial axis", Wikipedia, https://en.wikipdia.org/wiki/Medial_axis, last updated Apr. 1, 2021.
Moreo et al., "Modelling the mixed-mode failure of cement-bone interfaces", Engineering Fracture Mechanics, 2006, pp. 1379-1395, vol. 73.
Perez et al., "A comparative FEA of the debonding process in different concepts of cemented hip implants", Medical Engineering & Physics, 2006, pp. 525-533, vol. 28.
"Principal component analysis", Wikipedia, https://en.wikipedia.org/wiki/Principal_component_analysis, last updated Jun. 8, 2021.
Roque et al., "Mechanical Competence of Bone: A New Parameter to Grade Trabecular Bone Fragility from Tortuosity and Elasticity", IEEE Transactions on Biomedical Engineering, 2013, pp. 1363-1370, vol. 60, No. 5.
"Topological skeleton", Wikipedia, https://en.wikipedia.org/wiki/Topological_skeleton, last updated Oct. 29, 2020.

* cited by examiner

METHOD FOR OBTAINING AN IMAGE BIOMARKER THAT QUANTIFIES THE QUALITY OF THE TRABECULAR STRUCTURE OF BONES

CROSS-REFERENCE TO RELATED APPLICATIONS

This application is the United States national phase of International Application No. PCT/ES2020/070033 filed Jan. 17, 2020, and claims priority to Spanish Patent Application No. P201931050 filed Nov. 27, 2019, the disclosures of which are hereby incorporated by reference in their entirety.

BACKGROUND OF THE DISCLOSURE

Field of the Disclosure

The present disclosure is a method that enables an image biomarker that quantifies the quality of the trabecular structure, QTS ("Quality of Trabecular Structure"), to be obtained based on medical imaging from Computed Tomography (CT) and/or Magnetic Resonance Imaging (MRI) techniques which contain anatomical regions with a significant presence of bone trabeculae, generally wrist, vertebrae or the femoral head.

Description of Related Art

The most widely used technique for the study of Osteoporosis is dual-energy X-ray absorptiometry (DXA), a technique that provides measurements of bone mineral density (BMD), which is non-invasive, precise and reproducible, but which does not provide sufficient spatial information, resolution (it does not enable the trabecular microstructure to be observed) or dimensionality (mainly 2D) to become a complete diagnostic technique.

Other techniques such as high-resolution peripheral quantitative computed tomography (HR-pQCT) are making it possible to obtain images with a very high spatial resolution in vivo, reaching isotropic voxel sizes of up to 80 microns ($\mu m$), but in addition to using ionising radiation, these techniques only allow acquisition in distal extremities due to their small size.

Computed tomography (CT) makes it possible to assess both the cortical bone and some detail of the trabecular organisation, but the required radiation dose is not negligible and its maximum spatial resolution provides voxels of 250×250×500 $\mu m$, which are far from the level of detail required for the study of bone microarchitecture. Magnetic Resonance Imaging (MRI) is an imaging technique that does not use ionising radiation, with good spatial resolution and high contrast between bone and bone marrow. Traditionally, the use of MRI for studying bone has been limited due to the low intensity of bone tissue in the MRI images. This reduced signal intensity is due to the rapid loss of signal produced by the short relaxation time (250-500 $\mu s$) of the water found in the bone micropores next to the hydroxyapatite crystals (Kuhn et al., 1996). Modern high-field machines, such as the 3-Tesla MRI scanners, equipped with high-speed gradients and optimised coil design can provide very high spatial resolutions, on the order of 100 to 200 microns in all three spatial directions, maintaining a satisfactory signal-to-noise ratio (SNR). Several high spatial resolution MRI studies have already been performed in vivo for the study of microarchitecture in humans (Alberich-Bayarri et al., 2008).

Today, with the development that computers and various software have undergone, medical image processing and computer simulation have become necessary tools for research in the field of orthopaedics and bone mechanics. In the field of extraction of morphological image biomarkers, segmentation and contour detection techniques have made it possible to provide information with high added value for distinguishing patients with osteoporosis with a high degree of sensitivity (Alberich-Bayarri et al., 2010).

In the field of mechanical analysis, the most widely used tool is the Finite Element (FE) method (Burkhart et al., 2013). This method is applied to bone and soft tissue to predict deformations of musculoskeletal structures and explore the biophysical stimulus within tissues at the cellular level (Christen et al., 2010; Ascenzi and Reilly, 2011). The contribution of FE modelling to the scientific understanding of joint replacements has been extensively reviewed, especially in both cemented and uncemented total hip arthroplasty (Perez et al., 2006; Moreo et al., 2007).

Lastly, the incorporation of FE models for the simulation of adaptive biological processes opens up an important field of research, allowing scientists to test "rules" or "algorithms" for tissue growth, adaptation and degeneration (Gómez-Benito et al., 2006). There are more and more complex models, called multiscale models, that have been developed to connect the different scales (organ-tissue-cell-molecule) in the simulation of what happens in bone tissue (Hambli, 2011; Barkaoui et al., 2014).

SUMMARY OF THE DISCLOSURE

The present disclosure relates to a method for obtaining an image biomarker that quantifies the quality of the trabecular structure of bones. That is, by means of embodiments of the present disclosure, a biomarker that represents bone degeneration can be obtained from CT and/or MRI images of a patient who has not received any intervention.

In one embodiment, the method for obtaining an image biomarker that quantifies the quality of the trabecular structure of bones of the present disclosure comprises:
  retrieving high-resolution trabecular images generated by a technique selected from among Computed Tomography "CT", Magnetic Resonance Imaging "MRI" and a combination of "CT" and "MRI", wherein the high-resolution trabecular images come from a medical image database, preferably in DICOM ("Digital Imaging and Communications in Medicine") format, with a large quantity of content from trabecular regions;
  pre-processing the high-resolution trabecular images by means of the following sub-steps:
    obtaining a region of interest "ROI";
    calculating a bone fraction map;
    removing a partial volume effect;
    binarizing;
  post-processing the high-resolution trabecular images by means of the following sub-steps:
    skeletonisation; and,
    extraction of morphological and structural characteristics;
  obtaining a unique image biomarker "QTS":

$QTS = 0.7137 * Comp1 + 0.2863 * Comp2;$ where:

$Comp1 = BV/TV_1 * BV/TV + TbTh_1 * TbTh + TbSp_1 * TbSp + TbN_1 * TbN + D2D_1 * D2D + + D3D_1 * D3D;$ Comp2=BV/TV$_2$*BV/TV+TbTh$_2$*TbTh+
  TbSp$_2$*TbSp+TbN$_2$*TbN+D2D$_2$*D2D++
  D3D$_2$*D3D;

with

BV/TV$_1$=0.255; TbTh$_1$=−0.023; TbSp$_1$=−0.277;
  TbN$_1$=0.280; D2D$_1$=0.246; D3D$_1$=0.089;

BV/TV$_2$=0.331; TbTh$_2$=0.670; TbSp$_2$=0.066;
  TbN$_2$=0.123; D2D$_2$=−0.239; D3D$_2$=−0.292;

and,

BV/TV=(BV/TV−mean(BV/TV)/std.dev(BV/TV);

TbTh=(TbTh−mean(TbTh)/std.dev(TbTh);

TbSp=(TbSp−mean(TbSp)/std.dev(TbSp);

TbN=(TbN−mean(TbN)/std.dev(TbN);

D2D=(D2D−mean(D2D)/std.dev(D2D);

D3D=(D3D−media (D3D)/std.dev(D3D);

and considering that:
BV/TV: trabecular volume; TbTh: mean trabecular thickness; TbSp: mean trabecular separation; TbN: trabecular number; D2D: 2D fractal dimension; D3D: 3D fractal dimension; VARIABLE_NAME$_n$, where n=1, 2, is the respective VARIABLE_NAME value to calculate "Comp1" and "Comp2" respectively.

Particularly, the medical images with a large quantity of content from trabecular regions may be high-resolution trabecular images that represent a wrist, a femoral head or a vertebra of an individual.

In another embodiment, the method for obtaining an image biomarker that quantifies the quality of the trabecular structure of bones further comprises the retrieval of high-resolution CT trabecular images from the database which comply with the following parameters and their corresponding values:

| Parameter | Value |
| --- | --- |
| kVp | 120 |
| Tube Current (mAs) | <150 |
| Voxel size [mm] | <0.3 × 0.3 |
| Slice thickness [mm] | <0.3 |

In another embodiment, the method for obtaining an image biomarker that quantifies the quality of the trabecular structure of bones further comprises the retrieval of high-resolution MRI trabecular images from the database. The high-resolution MRI trabecular images are generated by magnetic resonance equipment with a static field strength of at least 3T and multi-element coils with parallel acquisition capability (specifically for the anatomical region that is to be covered), and that they comply with the following parameters and their corresponding values:

| Parameter | Value | Parameter | Value |
| --- | --- | --- | --- |
| Acquisition Mode | 3D | Phase Direction | A-P |
| TR [ms] (1.5T/3.0T) | 16 | Reconstructed matrix | 512x512 |
| TE [ms] (1.5T/3.0T) | 5 | Bandwidth [Hz/pix] | 220 |
| Flip angle (°) | 25 | Parallel image factor | 2 |
| Voxel size [mm] | <0.3 × 0.3 | Number of averages (NSA, NEX) | 3 |
| Slice thickness [mm] | <0.3 | Temporal Resolution | — |

In another embodiment, the first sub-step which refers to the calculation of the region of interest "ROI" of the second pre-processing step comprises the delimitation of a "region of interest" "ROI", which is obtained by detecting the trabecular areas. Moreover, the second sub-step, in which the bone fraction map of the second pre-processing step is calculated, comprises the elimination of heterogeneities in the scale of intensities of the high-resolution MRI trabecular image that contains the delimited ROI, applying a statistically-based local threshold algorithm, which determines the intensity value of the marrow in the vicinity of each voxel based on the statistics of the nearest neighbour, adjusting the threshold of the high-resolution MRI trabecular image and enabling the scaling of the intensity of the voxels partially occupied by trabecula, finally producing a bone volume fraction map. Moreover, the third sub-step, in which the partial volume effect is eliminated, comprises the division of each voxel into sub-voxels, which are assigned an intensity value according to the voxel itself and its neighbouring voxels with the condition that the quantity of intensity must be maintained. Preferably, each voxel is divided into equal (same size) sub-voxels. Moreover, the fourth sub-step of binarization comprises discretising the high-resolution trabecular images obtained from the third sub-step into binary code in such a way that the voxels representing the trabeculae are represented by "1's" and the voxels representing the bone marrow are represented by "0's", applying a bimodal threshold algorithm on the histogram of a volume, minimising the variance of intra-class intensities, obtaining a 3D binarized volume made up only of "1's" and "0's", representing the trabeculae and bone marrow, respectively. Moreover, the second sub-step of "extraction of morphological and structural characteristics comprises:

calculating, from the binarized volume, the trabecular volume "BV/TV" defined as the fraction or percentage between the number of voxels tagged as "1's" and the total number of voxels comprising the binarized volume;

calculating the mean trabecular thickness "TbTh" defined as the average of the thickness of all the trabeculae present in the binarized volume, and in order to do this, the contours of the binarized volume are detected and a 2D skeletonisation is carried out (consisting of iteratively eroding the object so that the voxels of its contour are removed without breaking the object) for each one of the slices; subsequently, using the distance-transforming method applied to each point of the skeleton, the minimum distance from each point to the contour is obtained and multiplied by two, in order to represent the thickness of the trabeculae at each point of the skeleton; lastly, it is averaged, adding all of the distances stored at each point of the skeleton and dividing by the number of points contained in the skeleton, obtaining the mean trabecular thickness "TbTh";

calculating the mean trabecular separation "TbSp", which is done by repeating the previous two steps, but starting from an inverted binarized volume;

calculating the trabecular number "TbN" using the following equation:

$$TbN = \frac{BV/TV}{TbTh} \quad \text{(equation 1)}$$

calculating the 2D fractal dimension "D2D", which requires:
  obtaining the contour of the surface to be characterised;
  applying an initial mesh to the surface to be characterised, where each of the plots contains contours;
  reducing the size of each side of the plot by half;
  repeating the reduction of the matrix size iteratively until the pixel size is reached;
  solving the equation:

$$\log(N) = -D^{2D} \cdot \log(\lambda) + k \quad \text{(equation 2)}$$

where equation 2 represents the ratio between the number of plots "N" corresponding to a size "λ", the 2D fractal dimension "D2D" and a proportionality constant;

calculating the 3D fractal dimension "D3D", which requires:
  obtaining the 3D volume to be characterised;
  applying an initial mesh of cubes on the surface to be characterised;
  reducing the size of the cubes iteratively until the size of the voxel is reached;
  solving the equation:

$$\log(N) = -D^{3D} \cdot (\lambda) + k \quad \text{(equation 3)}$$

In summary, for each study, an assessment is made of bone quality, and the extracted parameters (BV/TV, TbTh, TbSp, TbN, D2D and D3D). Therefore, for N analysed studies, the corresponding assessments of bone quality and the extracted parameters thereof are obtained (BV/TV, TbTh, TbSp, TbN, D2D and D3D). The object of the method of the present disclosure is therefore to have only one parameter ("QTS") that correlates with the bone quality assessment, instead of having six parameters (BV/TV, TbTh, TbSp, TbN, D2D and D3D). To do this, by means of a principal component analysis, it is found that the information provided by the six parameters extracted from each study can be expressed with just two parameters "Comp1" and "Comp2", each multiplied by a coefficient (0.7137 and 0.2863). Each one of these new parameters, "Comp1" and "Comp2", are generated as a linear combination of the six extracted parameters. That is, if BV/TV is multiplied by a specific value/coefficient+TbTh by another specific value/coefficient+TbSp by another specific value/coefficient+TbN by another specific value/coefficient+D2D by another specific value/coefficient+D3D by another specific value/coefficient, Comp1 is obtained. These coefficients, in the present disclosure, have been named as "name of parameter1". That is, BV/TV1, TbTh1, TbSp1, TbN1, D2D1, D3D1, In the same way, but with other coefficients, the parameter "Comp2" is obtained. Multiplying the parameters "Comp1" and "Comp2" by their respective coefficients and adding the result of both multiplications, the quality of the trabecular bone "QTS" is obtained.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

The embodiments of the disclosure in relation to the figures are described below.

Figure 1:
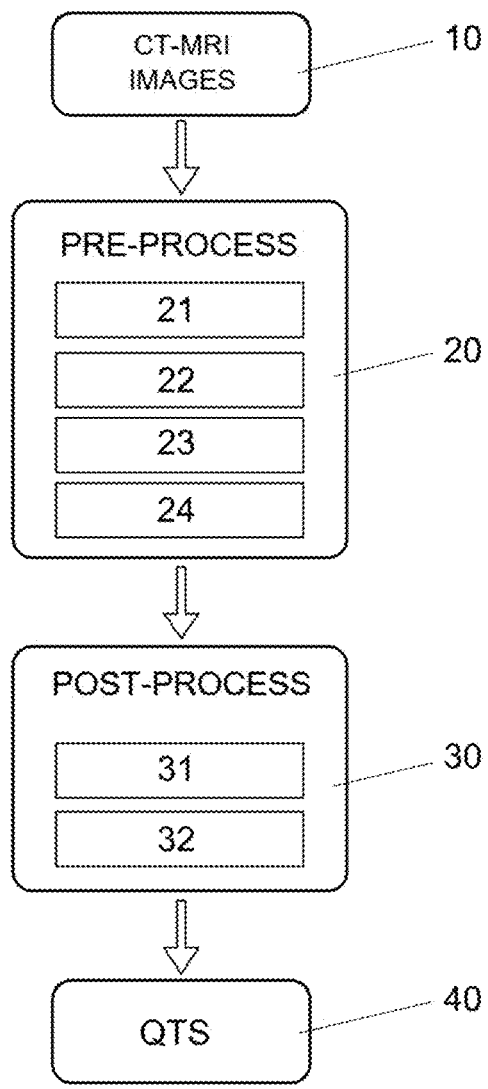
FIG. 1 shows a flow chart of the steps of the method for obtaining an image biomarker that quantifies the quality of the trabecular structure of bones of the present disclosure.

FIG. 1 shows the method of the present disclosure, where the different steps required to obtain the QTS (Quality of Trabecular Structure) image biomarker are shown.

Initially, it involves retrieving images from a medical image database, preferably in DICOM format. Currently, the images captured by medical devices are archived and transmitted through the "PACS" (Picture Archiving and Communication System). PACS is a computerised system for digital archiving of medical images (nuclear medicine, computed tomography, ultrasound, mammography, etc.) and for the transmission of these images to dedicated display stations or between these stations via a computer network. Therefore, the first step of the method 10 is the retrieval of high-resolution CT (Computed Tomography) and MRI (Magnetic Resonance Imaging) images from the medical image database.

The high-resolution CT images must fulfil several minimum parameters which are shown in the following table (Table 1).

TABLE 1

| | |
|---|---|
| kVp | 120 |
| Tube Current (mAs) | <150 |
| Voxel size [mm] | <0.3 × 0.3 |
| Slice thickness [mm] | <0.3 |

The high-resolution MRI images must fulfil several minimum parameters which are shown in the following table (Table 2). The high-resolution MRI images must have been generated by clinical magnetic resonance equipment with a static field strength greater than or equal to 3T and multi-element coils with parallel acquisition capacity specific to the anatomical region to be covered.

TABLE 2

| Acquisition Mode | 3D | Phase Direction | A-P |
|---|---|---|---|
| TR [ms] (1.5T/3.0T) | 16 | Reconstructed matrix | 512x512 |
| TE [ms] (1.5T/3.0T) | 5 | Bandwidth [Hz/pix] | 220 |
| Flip angle (°) | 25 | Parallel image factor | 2 |
| Voxel size [mm] | <0.3 × 0.3 | Number of averages (NSA, NEX) | 3 |
| Slice thickness [mm] | <0.3 | Temporal Resolution | — |

Preferably, high-resolution CT and MRI images must contain the largest quantity of trabeculae. The largest quantity of trabeculae is concentrated in the regions indicated in Table 3.

TABLE 3

| Wrist | Level of distal metaphysis of the radius |
|---|---|
| Femoral Head | Metaphysis, femoral head and neck |
| Vertebra | Vertebra body |

Once the high-resolution CT and MRI images have been retrieved 10, pre-processing 20 and post-processing 30, which are explained below, are applied.

Figure 2:
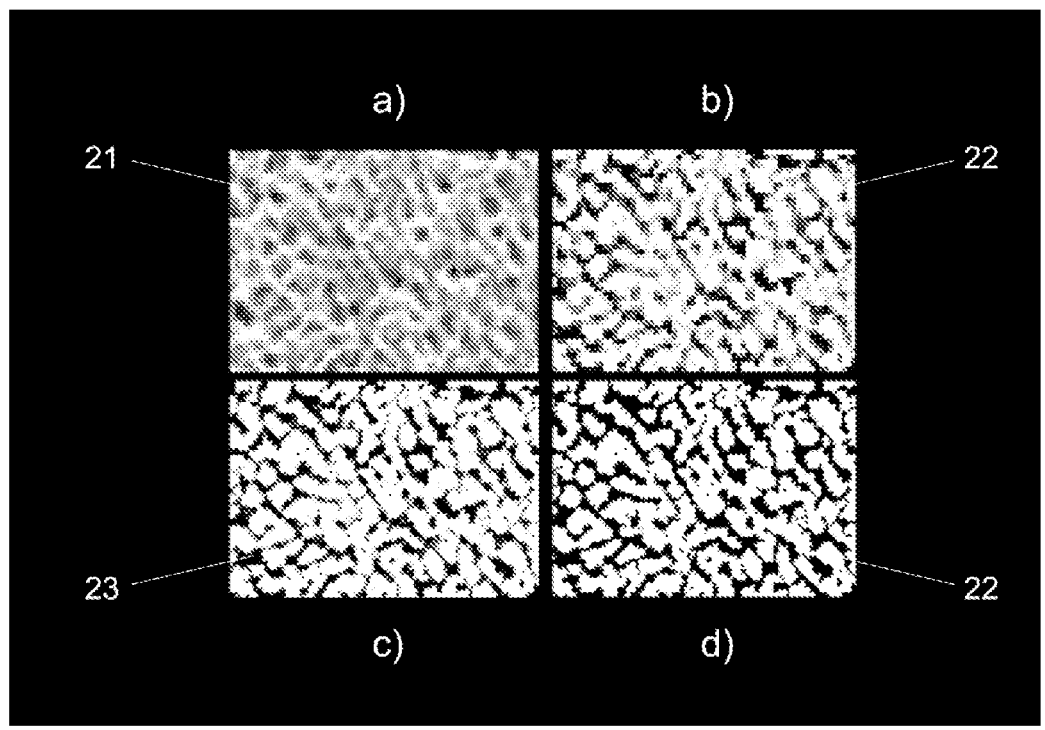
FIG. 2(a) shows, within the step of pre-processing the retrieved high-resolution CT and/or MRI images, on the region of interest "ROI", which exclusively contains trabeculae (dark) and bone marrow (bright).
FIG. 2(b) shows, within the step of pre-processing the retrieved high-resolution CT and/or MRI images, the calculation of the bone fraction map after the correction of heterogeneities, where the intensity of the voxel is proportional to the quantity of bone contained in the voxel.
FIG. 2(c) shows, within the step of pre-processing the retrieved high-resolution CT and/or MRI images, an interpolated image after increasing the resolution to eliminate partial volume effects.
FIG. 2(d) shows, within the step of pre-processing the retrieved high-resolution CT and/or MRI images, the binary discretisation, where the voxels have been classified into trabeculae (white) and marrow (black).

Therefore, the second step of the method of the present disclosure is to pre-process 20 the retrieved high-resolution CT and/or MRI images. This second step of the method in turn comprises four sub-steps which are listed below:

Obtaining 21 the region of interest "ROI" (FIG. 2a);
Calculating 22 the bone fraction map (FIG. 2b);
Removing 23 the partial volume effect (FIG. 2c);
Binarizing 24 (FIG. 2d).

The first sub-step 21 in which the region of interest "ROI" (FIG. 2a) of the second step, pre-processing 20, is obtained consists of the delimitation of the "region of interest" "ROI", which must contain only trabecular volume. To calculate the trabecular volume, the contour of the trabeculae must be calculated. To calculate the contour of the trabecula, the internal contour of the cortical bone is traced. The internal contour of the cortical bone is obtained by detecting the areas in which a large variation in intensity is observed for those same voxels in adjacent slices.

The second sub-step 22 in which the bone fraction map (FIG. 2b) of the second step, pre-processing 20, is calculated consists of the elimination of the heterogeneities in the scale of intensities of the MRI image containing the delimited ROI. Due to the high resolution of the MRI images, slight intensity modulations are produced by small local field inhomogeneities in MRI. This means that voxels belonging to the same class located in different regions of the volume may be classified into different classes because they present different signal intensities, resulting in erroneous detection of the bone trabeculae in the subsequent binarization substep. To correct it, a statistically-based local threshold algorithm is applied, which determines the intensity value of the marrow in the vicinity of each voxel based on the statistics of the nearest neighbour. This adjusts the threshold of the image and enables the scaling of the intensity of the voxels partially occupied by trabecula, finally producing a bone volume fraction map. This step is not necessary in the case of CT images.

The third sub-step 23 in which the partial volume effect (FIG. 2c) is eliminated consists of dividing each voxel into sub-voxels, which are assigned an intensity value according to the voxel itself and its neighbours, under the assumption that the quantity of intensity must be maintained. The partial volume effect is shown as a blurring on the images which is produced as a result of the spatial variation of the sample, which is comparable in magnitude to the resolution used during high-resolution CT and MRI imaging. The use of a resolution on the same order or higher than the structure to be acquired together with a low signal-to-noise ratio due to the high-resolution causes the intensity of each voxel to represent the bone fraction contained in the bone itself, which means that the third sub-step described increases the reconstructed spatial resolution. Preferably, each voxel is divided into 8 sub-voxels, which are assigned an intensity value according to the voxel itself and its neighbours, under the assumption that the quantity of intensity must be maintained. The increased resolution after this sub-step results in a filtered volume and isometric voxels (if the original voxel was already isometric; otherwise the voxels would not be isometric), which indicate the bone fraction that occupies them with a level of intensity. It is important to note that if a voxel is divided into 8 sub-voxels, each of these will be half the size of the original in each of its three spatial dimensions.

The fourth sub-step 24 of binarization (FIG. 2d) consists of discretising the high-resolution images obtained from the third sub-step into binary code in such a way that the voxels representing the trabeculae are represented by "1's" and the voxels representing the bone marrow are represented by "0's", That is, it applies a bimodal thresholding method based on minimisation of intra-class variance, to select only those voxels corresponding to bone trabecula. The method is implemented on the 3D volume histogram, minimising the variance of intra-class intensities, which maximises the variance between classes. The result is a logical 3D volume made up of only "1's" and "0's", representing the trabeculae and bone marrow, respectively. The 3D logical volume composed of only "1's" and "0's" is called a "binarized volume".

After pre-processing 20, the post-processing 30 is applied. Therefore, the third step of the method of the present disclosure is to post-process 30 the retrieved high-resolution CT and/or MRI images.

This third step 30 of the method in turn comprises four sub-steps which are listed below:

Skeletonisation 31; and,
Extraction of morphological and structural characteristics 32.

Figure 3:
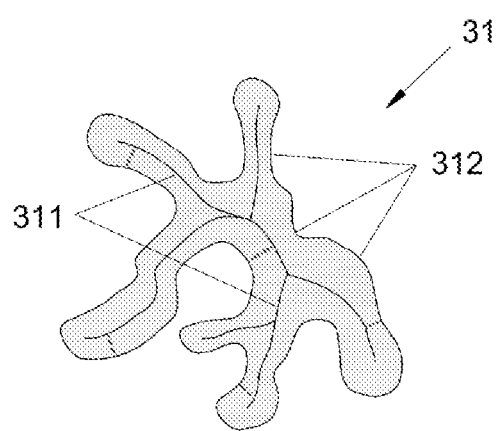
FIG. 3 shows, within the step of post-processing the retrieved high-resolution CT and/or MRI trabecular images, the result of "skeletonisation", the thinner line that preserves the connectivity and shape of an object without breaking it superimposed on the contour of the trabecula.

The purpose of the first sub-step 31 of "skeletonisation" is to produce the connected internal structure with the smallest thickness of an object, preserving its topology and maintaining the shape of the object as much as possible. Skeletonisation, see FIG. 3, consists of iteratively eroding the object so that the voxels of its contour are eliminated without breaking the object. FIG. 3 shows the skeleton 311, the thinner line that preserves the connectivity and shape of an object without breaking it. FIG. 3 also shows the contour 312 that surrounds the skeleton.

Figure 4:
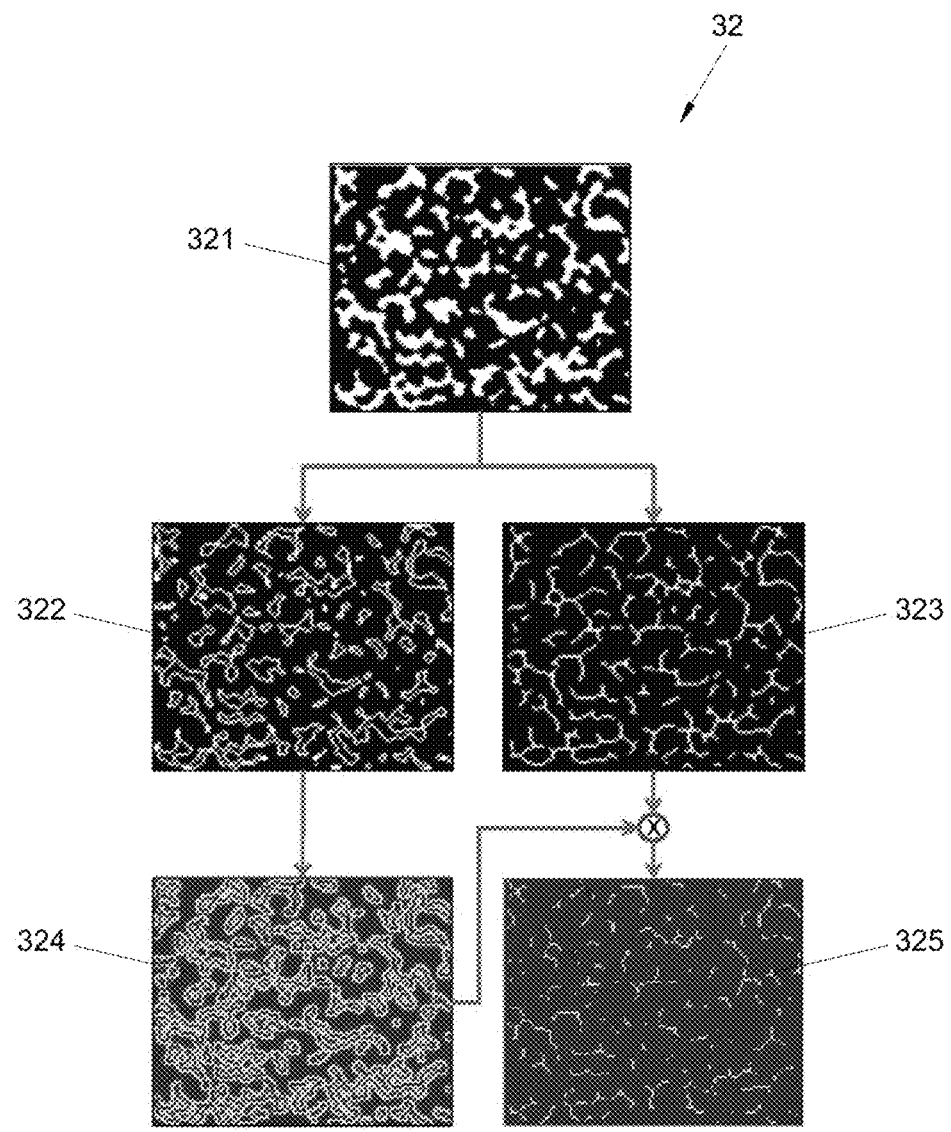
FIG. 4 shows the diagram of obtaining the trabecular thickness from a binarized volume.

The second sub-step 32 of "extraction of morphological and structural characteristics" serves to structurally characterise the bone trabecula. The structural characterisation of the bone trabeculae is largely determined by the extraction of the trabecular volume or percentage of bone volume in relation to the total volume under analysis (BV/TV, "Bone Volume to Total Volume") and other morphological parameters, such as the mean trabecular thickness (TbTh), the mean trabecular separation (TbSp) or trabecular pore size and trabecular number (TbN) or trabecular index. The trabecular volume BV/TV is obtained as the fraction or percentage between the number of voxels tagged as "1's", in the logical volume obtained in the previous step, and the total number of voxels that make up the logical volume. The mean trabecular thickness "TbTh" represents the average of the thickness of all the trabeculae present in the volume. The process of obtaining the mean trabecular thickness is shown in FIG. 4. To do this, starting with the binarized volume 321, the contours of the binarized volume are detected 322 and a 2D skeletonisation is performed 323 for each of the slices. Subsequently, the distance-transforming method is applied 324 to the entire slice, and this transformation is multiplied by the skeleton, thereby obtaining the minimum distance from each point to the contour 325. Multiplying this minimum distance by two, the trabecular thickness for each point of the skeleton is obtained. Finally, adding up the trabecular thickness obtained for each point of the skeleton and dividing it by the number of voxels that make up the skeleton, the mean trabecular thickness is obtained. The mean trabecular separation TbSp is determined by the pore size, or average thickness of the bone marrow present between trabeculae, which means that the process of obtaining the mean trabecular separation is complementary to the process of obtaining the mean trabecular thickness. In order to obtain it, the binarized volume is inverted and the previous process is applied. The trabecular number TbN gives an idea of the number of trabeculae present in the volume, so, in order to obtain it, the ratio between the volume of trabeculae present in the volume and the mean trabecular thickness is established, by applying equation 1:

$$TbN = \frac{BV/TV}{TbTh} \quad \text{(equation 1)}$$

Figure 5:
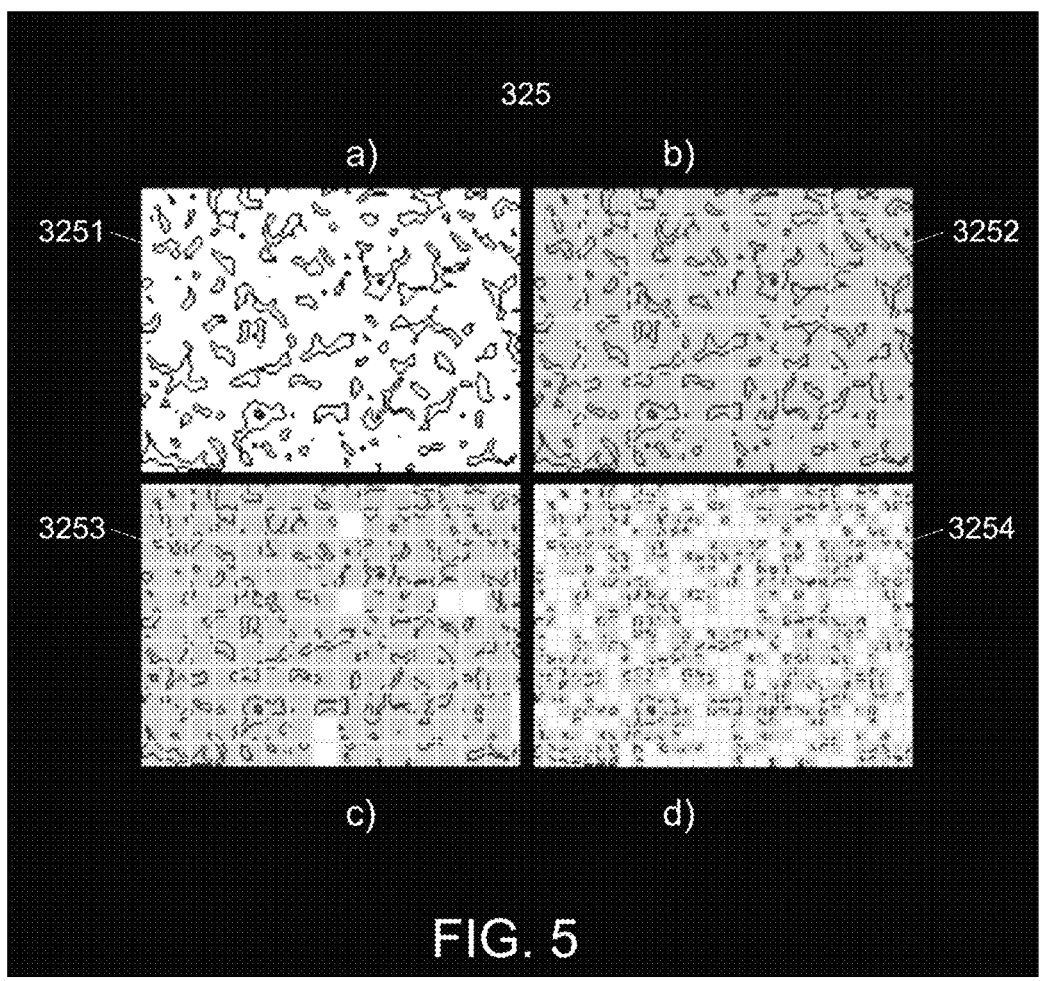
FIG. 5 shows the process described for calculating the 2D fractal dimension, where: (a) shows the contours of the trabeculae on the surface to be characterised; (b) shows an initial meshing of the surface; (c) after reducing the size of each plot side by half, six plots that do not contain any contours are found; and, (d) reducing the side of each plot by half again, multiple plots that do not contain contours appear.

The fractal characterisation of structures makes it possible to quantify the spatial irregularities of the formation of complex structures, presenting a significant correlation with its fracture resistance and the direction of crack propagation, which means that obtaining it is important to determine trabecular bone quality. In the present method, a 2D and a 3D focus have been implemented for the in vivo characterisation of the trabecular structure. For the 2D approach, a conventional square or plot counting algorithm is used which consists firstly, of obtaining the contour of the structure, slice by slice, with each slice then divided into smaller plots in each iteration, collecting the number of plots containing a contour for each iteration in a vector, as shown in FIG. 5. FIG. 5 shows the process described for the calculation of the 2D fractal dimension, first, (FIG. 5a) the contour 3251 of the surface to be characterised is obtained. Subsequently, an initial meshing 3252 of the surface is carried out (FIG. 5b), where each of the plots contains contours. After reducing 3253 the size of each side of the plot by half (FIG. 5c), six plots that do not contain any contours are found. Reducing 3254 the side of each plot by half again (FIG. 5d) multiple plots that do not contain contours appear.

Lastly, using a least squares adjustment, the value of the 2D fractal dimension 325 is obtained by following equation 2:

$$\log(N) = -D^{2D} \cdot \log(\lambda) + k \quad \text{(equation 2)}$$

Equation 2 represents the ratio between the number of plots (N) corresponding to a size ($\lambda$), 2D fractal dimension and a proportionality constant.

The same analysis methodology for calculating the 2D fractal dimension has been extrapolated to the 3D fractal dimension by means of cube counting in this case. The number of cubes that contain trabeculae are stored in a vector and finally, by means of the least squares adjustment method, the 3D fractal dimension is cleared.

With the steps described above, the values BV/TV, TbTh, TbSp, TbN, D2D (2D fractal dimension) and D3D (3D fractal dimension) of a CT and/or MRI study of the regions indicated in Table 3 are obtained. In order to obtain an image biomarker that quantifies the quality of the trabecular structure "QTS", a principal components multivariate analysis is applied to the set of parameters extracted for a set of N studies analysed from the same region ("ROI"). The purpose of which is to reduce the dimensionality of the set of extracted parameters (BV/TV, TbTh, TbSp, TbN, D2D and D3D) to a single parameter that quantifies the quality of the trabecular structure referred to in the present disclosure as "QTS".

Therefore, the last step of the method is performed after extracting the previous parameters (BV/TV, TbTh, TbSp, TbN, D2D and D3D) from a sample of N studies.

To do this, first, the previously extracted parameters are normalised and centred, by subtracting the mean value (expressed mathematically as "mean(X)") and dividing by the standard deviation (expressed mathematically as "std.dev(X)") of each parameter.

BV/TV=(BV/TV−mean(BV/TV)/std.dev(BV/TV);

TbTh=(TbTh−mean(TbTh)/std.dev(TbTh);

TbSp=(TbSp−mean(TbSp)/std.dev(TbSp);

TbN=(TbN−mean(TbN)/std.dev(TbN);

D2D=(D2D−mean(D2D)/std.dev(D2D);

D3D=(D3D−mean(D3D)/std.dev(D3D);

After normalising the parameters, by studying the correlation matrix of the aforementioned parameters, two main components or principal factors are obtained, which have been named "Comp1" and "Comp2", such that "Comp1" represents the largest proportion of original variability and "Comp2" the maximum possible variability not represented by "Comp1". Each of these principal factors is expressed as a linear combination of the original parameters with weight VARIABLE_NAME$_n$, n=1,2 being for "Comp1" and "Comp2", respectively, as shown in the following equation.

Comp1=BV/TV$_1$*BV/TV+TbTh$_1$*TbTh+
  TbSp$_1$*TbSp+TbN$_1$*TbN+D2D$_1$*D2D++
  D3D$_1$*D3D;

Comp2=BV/TV$_2$*BV/TV+TbTh$_2$*TbTh+
  TbSp$_2$*TbSp+TbN$_2$*TbN+D2D$_2$*D2D++
  D3D$_2$*D3D;

with
BV/TV$_1$=0.255;
TbTh$_1$=−0.023;
TbSp$_1$=−0.277;
TbN$_1$=0.280;
D2D$_1$=0.246;
D3D$_1$=0.089;
BV/TV$_2$=0.331;
TbTh$_2$=0.670;
TbSp$_2$=0.066;
TbN$_2$=0.123;
D2D$_2$=−0.239;
D3D$_2$=−0.292;

The values for each of the coefficients indicated above may vary in significantly different populations, and they may even undergo slight variations as the study sample is enlarged.

Lastly, the unique image biomarker that expresses the quality of the trabecular bone "QTS" is obtained by the final equation:

$$QTS=0.7137*Comp1+0.2863*Comp2.$$

The invention claimed is:

1. A method for obtaining an image biomarker that quantifies the quality of the trabecular structure of bones, the method comprising:
retrieving high-resolution trabecular images generated by a technique selected from among Computed Tomography (CT), Magnetic Resonance Imaging (MRI) and a combination of CT and MRI, wherein the high-resolution trabecular images are retrieved from a medical image database with a large quantity of content from trabecular regions;
pre-processing the high-resolution trabecular images, wherein pre-processing the high-resolution trabecular images comprises:
obtaining a region of interest (ROI);
calculating a bone fraction map;
removing a partial volume effect; and
binarizing;
post-processing the high-resolution trabecular images, wherein post-processing the high-resolution trabecular images comprises:
skeletonisation; and
extracting morphological and structural characteristics; and
obtaining a unique image biomarker (QTS) based on the following equation:

$$QTS=0.7137*Comp1+0.2863*Comp2,$$

where:

$$Comp1=BV/TV_1*BV/TV+TbTh_1*TbTh+TbSp_1*TbSp+TbN_1*TbN+D2D_1*D2D+D3D_1*D3D;$$

$$Comp2=BV/TV_2*BV/TV+TbTh_2*TbTh+TbSp_2*TbSp+TbN_2*TbN+D2D_2*D2D+D3D_2*D3D,$$

where:

$$BV/TV_1=0.255; TbTh_1=-0.023; TbSp_1=-0.277; TbN_1=0.280; D2D_1=0.246; D3D_1=0.089;$$

$$BV/TV_2=0.331; TbTh_2=0.670; TbSp_2=0.066; TbN_2=0.123; D2D_2=-0.239; D3D_2=-0.292,$$

and
where:

$$BV/TV=(BV/TV-mean(BV/TV)/std.dev(BV/TV);$$

$$TbTh=(TbTh-mean(TbTh)/std.dev(TbTh);$$

$$TbSp=(TbSp-mean(TbSp)/std.dev(TbSp);$$

$$TbN=(TbN-mean(TbN)/std.dev(TbN);$$

$$D2D=(D2D-mean(D2D)/std.dev(D2D);$$

$$D3D=(D3D-mean(D3D)/std.dev(D3D),$$

wherein
BV/TV is associated with a trabecular volume; TbTh is associated with a mean trabecular thickness; TbSp is associated with a mean trabecular separation; TbN is associated with a trabecular number; D2D is associated with a 2D fractal dimension; D3D is associated with a 3D fractal dimension; and VARIABLE_NAME$_n$, where n=1,2, is the respective VARIABLE_NAME value to calculate "Comp1" and "Comp2" respectively.

2. The method for obtaining an image biomarker that quantifies the quality of the trabecular structure of bones, according to claim 1, further comprising:
retrieving high-resolution CT trabecular images with the following parameters and corresponding values: kVp=120, Tube Current (mAs)<150, Voxel size in millimetres (mm).<150, and Slice Thickness in millimetres (mm)<0.03.

3. The method for obtaining an image biomarker that quantifies the quality of the trabecular structure of bones, according to claim 1, further comprising:
retrieving high-resolution MRI trabecular images by magnetic resonance equipment with a static field strength of at least 3T and multi-element coils with parallel acquisition capability,
wherein the magnetic resonance equipment comply with the following parameters and corresponding values: Acquisition Mode=3D, TR (in milliseconds) (1.5T/3.0T)=16, TE (in milliseconds) (1.5T/3.0T)=5, Flip angle (°)=25, Voxel size (in millimetres)<(0.3×0.3), Slice thickness (in millimetres)<0.3, Phase Direction=A–P, Reconstruction Matrix=512×512, Bandwidth (Hz/pix)=220, Parallel image factor=2, and Number of averages (NSA.NEX)=3.

4. The method for obtaining an image biomarker that quantifies the quality of the trabecular structure of bones, according to claim 1, wherein the medical images with a large quantity of content from trabecular regions represent a wrist, a femoral head or a vertebra of an individual.

5. The method for obtaining an image biomarker that quantifies the quality of the trabecular structure of bones, according to claim 2, wherein obtaining the ROI comprises:
delimiting the ROI, which is obtained by detecting the trabecular regions.

6. The method for obtaining an image biomarker that quantifies the quality of the trabecular structure of bones, according to claim 5, wherein calculating the bone fraction map comprises:
eliminating heterogeneities in a scale of intensities of the high-resolution MRI trabecular image that contains the ROI that was delimited,
applying a statistically-based local threshold algorithm, which determines an intensity value of marrow in a of each voxel based on the statistics of the nearest neighbour,
adjusting the threshold of the high-resolution MRI trabecular image and enabling the scaling of the intensity of the voxels partially occupied by trabecula, and
producing a bone volume fraction map.

7. The method for obtaining an image biomarker that quantifies the quality of the trabecular structure of bones, according to claim 5, wherein removing the partial volume effect comprises:
dividing each voxel into sub-voxels, which are assigned an intensity value according to the voxel itself and its neighbouring voxels with the condition that a quantity of intensity must be maintained.

8. The method for obtaining an image biomarker that quantifies the quality of the trabecular structure of bones, according to claim 7, wherein each voxel is divided into equal sub-voxels.

9. The method for obtaining an image biomarker that quantifies the quality of the trabecular structure of bones, according to claim 7, wherein binarization comprises:
- discretising the high-resolution trabecular images obtained from removing the partial volume effect into binary code in such a way that the voxels representing the trabeculae are represented by "1's" and the voxels representing bone marrow are represented by "0's";
- applying a bimodal threshold algorithm on a histogram of a volume;
- minimising a variance of intra-class intensities; and
- obtaining a 3D binarized volume made up only of "1's" and "0's".

10. The method for obtaining an image biomarker that quantifies the quality of the trabecular structure of bones, according to claim 1, wherein skeletonisation comprises:
- iteratively eroding an object so that voxels of a contour of the object are eliminated without breaking the object.

11. The method for obtaining an image biomarker that quantifies the quality of the trabecular structure of bones, according to claim 9, wherein extracting morphological and structural characteristic comprises:
- calculating, from the binarized volume, BV/TV defined as the fraction or percentage between a number of voxels tagged as "1's" and a total number of voxels comprising the binarized volume;
- calculating the TbTh defined as the average of the thickness of all the trabeculae present in the binarized volume based on:
  - detecting contours of the binarized volume;
  - performing a 2D skeletonization for each of the slices;
  - using a distance-transforming method applied to each point of the skeleton based on performing the 2D skeletonization for each of the slices, the minimum distance from each point to a contour being obtained and multiplied by two, in order to represent the thickness of the trabeculae at each point of the skeleton; and
  - adding all of the distances stored at each point of the skeleton and dividing by the number of points contained in the skeleton to obtain the TbTh,
- calculating TbSp by repeating the previous two steps, but starting from an inverted binarized volume; and
- calculating the TbN using the following equation:

$$TbN = \frac{BV/TV}{TbTh} \quad \text{(equation 1)}$$

- calculating the D2D, wherein calculating the D2D comprises:
  - obtaining the contour of the surface to be characterised;
  - applying an initial mesh to the surface to be characterised, where each plot contains contours;
  - reducing the size of each side of the plots by half;
  - repeating reduction of a matrix size iteratively until a pixel size is reached; and
  - solving a first equation:

$$\log(N) = -D^{2D} \cdot \log(\lambda) + k$$

where the first equation represents a ratio between a number of plots N corresponding to a size λ, the D2D and a proportionality constant; and
- calculating the D3D, wherein calculating the D3D comprises:
  - obtaining the 3D volume to be characterised;
  - applying an initial mesh of cubes on the surface to be characterised;
  - reducing the size of the initial mesh of cubes iteratively until the size of the voxel is reached; and
  - solving a second equation:

$$\log(N) = -D^{3D} \cdot \log(\lambda) + k.$$

* * * * *